(12) United States Patent
Rook

(10) Patent No.: US 7,052,685 B1
(45) Date of Patent: May 30, 2006

(54) METHODS FOR TREATMENT OF CUTANEOUS T-CELL LYMPHOMA

(75) Inventor: Alain H. Rook, Wynnewood, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 796 days.

(21) Appl. No.: 09/419,328

(22) Filed: Oct. 15, 1999

Related U.S. Application Data

(60) Provisional application No. 60/104,342, filed on Oct. 15, 1998.

(51) Int. Cl.
*A61K 45/00* (2006.01)

(52) U.S. Cl. .................... 424/85.2; 424/85.4; 424/85.1

(58) Field of Classification Search ............... 424/85.1, 424/85.2, 85.4, 85.5, 85.7; 514/2, 12, 885, 514/886
See application file for complete search history.

(56) References Cited

OTHER PUBLICATIONS

S. L. Lee et al. The regulation and biological activity of interleukin-12. May 1998. Leukemia and Lymphoma, 29(5-6): 427-38.*

T. Osaki et al. IFN-gamma-inducing factor/IL-18 administation mediates IFN-gamma and IL-12-independent antitumor effects. Feb. 15, 1998, J. Immunol., 160:1742-1749.*

Brunda, et al., "Antitumor and Antimetastatic Activity of Interleukin 12 against Murine Tumors", *J. Exp. Med.* 1993 178:869-879.

Diamandidou, E., et al., "Mycosis Fungoides and Sezary Syndrome", *Blood* 1996 88:2385-2409.

Haku, et al., "Interleukin-12-Mediated Killer Activity in Lung Cancer Patients", *Cytokine* 1997 9:846-852.

Hiramatsu, K., et al., "Generation of killer activity by interleukin-12 of mononuclear cells in malignant pleural effusions due to lung cancer", *Cancer Immunol. Immunother.* 1998 46:1-6.

Hsieh, C.S., et al., "Development of $T_H1$ $CD4^+$ T Cells Through IL-12 Produced by Listeria-Induced Macrophages", *Science* 1993 260:547-549.

Nishimura, et al., "Systemic in vivo antitumor activity of interleukin-12 against both transplantable and primary tumor", *Immunol. Lett.* 1995 48:149-152.

Rook, et al., "Interleukin-12 Therapy of Cutaneous T-Cell Lymphoma Induces Lesion Regression and Cytotoxic T-Cell Responses", *Blood* 1999 94:902-908.

Rook, et al., "The Immunopathogenesis of Cutaneous T-Cell Lymphoma", *Arch. Dermatol.* 1993 129:486.

Rook, et al., "IL-12 Reverses Cytokine and Immune Abnormalities in Sezary Syndrome[1]", *J. Immunol.* 1995 154:1491-1498.

Rook, et al., "The Potential Therapeutic Role of Interleukin-12 in Cutaneous T-Cell Lymphoma[cs]", *Ann. NY Acad. Sci.* 1996 795:310-318.

Rook, et al., "Pathogenesis of cutaneous T-cell lymphoma: implications for the use of recombinant cytokines and photopheresis", *Clin. Ex. Immunol.* 1997 107:16-20.

Sahin, et al., "Interleukin-12 increases bispecific-antibody-mediated natural killer cell cytotoxicity against human tumors", *Cancer Immunol. Immunother.* 1996 42:9-14.

Seo N., et al., "Tumour-specific cytotoxic T lymphocyte activity in Th2-type Sezary syndrome: its enhancement by interferon-gamma (IFN-γ) and IL-12 and fluctuations in association with disease activity", *Clin. Exp. Immunol.* 1998 112:403-409.

Verbik, et al., "In vivo therapeutic effects of interleukin-12 against highly metastatic residual lymphoma", *Clin. Exp. Metastasis* 1996 42:219-229.

Vowels, et al., "Aberrant Cytokine Production by Sezary Syndrome Patients: Cytokine Secretion Pattern Resembles Murine Th2 Cells", *J. Invest. Dermatol.* 1992 99:90-94.

Vowels, et al., "Th2 cytokine mRNA Expression in Skin in Cutaneous T-Cell Lymphoma", *J. Invest. Dermatol.* 1994 103:669-673.

Vowels, et al., "Normalization of Cytokine Secretion Patterns and Immune Function Following Disappearance of Malignant Clone from the Peripheral Blood of a Sezary Syndrome (SzS) Patient", *J. Invest. Dermatol.* 1993 100:556.

* cited by examiner

*Primary Examiner*—Brenda Brumback
*Assistant Examiner*—Dong Jiang
(74) *Attorney, Agent, or Firm*—Licata & Tyrrell P.C.

(57) ABSTRACT

A method and composition for treatment of advanced cutaneous T cell lymphoma is provided which involves administration of recombinant interleukin-12.

1 Claim, No Drawings

METHODS FOR TREATMENT OF CUTANEOUS T-CELL LYMPHOMA

INTRODUCTION

This application claims the benefit of priority from Provisional Application Ser. No. 60/104,342, filed Oct. 15, 1998.

BACKGROUND OF THE INVENTION

Cutaneous T-cell lymphoma (CTCL) is a lymphoproliferative disorder typically characterized by infiltration of the skin with clonally derived malignant CD4+ T lymphocytes that phenotypically resemble mature T cells (Diamandidou, E. et al. 1996. Blood 88:2385–2409). Early presentation of the disease may be confused with eczema, tinea corpus, or psoriasis. Therapeutic efforts are based on the extent of disease, the integrity of the immune system, and the likelihood for progression of disease. Several additional observations which can effect therapeutic decisions include 1) antitumor immune responses mediated by cytotoxic T cells detected in patients with CTCL, 2) biologic response modifiers, which can augment cytotoxic T-cell responses with other specific arms of the antitumor response, such as recombinant interferon-α, are therapeutically active in CTCL, and 3) combinations of potent chemotherapeutic agents do not appear to cure patients with early disease and do not prolong the survival of patients with advanced disease.

For patients with limited or early stage disease, the cell-mediated immune response is usually normal, and the likelihood for serious systemic disease progression is low. Accordingly, these patients can be treated effectively with a variety of skin-based therapies, including topical mechlorethamine, topical carmustine, and psoralen and ultraviolet A light (PUVA). A significant percentage of patients with such early disease appear to be cured of their disease with these treatments.

Advanced forms of CTCL are not as easily cured, and are often fatal. The patient with advanced forms of CTCL may present with malignancies that progress from plaques to tumors. A more common form of advanced CTCL, Sezary Syndrome (SzS), involves erythroderma occurring throughout the course of disease. In SzS, the malignant cell population, which has an early propensity to localize within the upper dermis, and particularly, within the epidermis (epidermotropism), also becomes nonepidermotropic and is associated with deeper dermal extension and involvement of the peripheral blood. Concurrent with this leukemic, progressive phase of the disease is the onset of progressive immunologic dysfunction. Among the constellation of immune abnormalities that have been noted are increased serum IgE, decreased T cell responses to antigens, impaired cellular cytotoxicity, and peripheral eosinophilia. Associated with these immune abnormalities is a striking deficiency in the ability of peripheral blood mononuclear cells (PBMC) to produce interferon-γ and interleukin-2 in response to activation signals (Rook, A. H. et al. 1993. Arch. Dermatol. 129:486; Vowels, B. R. et al. 1992. J. Invest. Dermatol. 99:90). In contrast to a defect in production of T-helper type 1 (Th1) cytokines, upon stimulation, PBMC from patients with SzS produce increased concentrations of interleukin-4, the levels of which correlate with numbers of circulating malignant T cells (Vowels, B. R. et al. 1992. J. Invest. Dermatol. 99:90). The ability to detect T-helper type 2 (Th2) cytokine mRNA (mRNA for interleukin-4 and interleukin-5) in skin lesions of patients with CTCL, but not in normal skin (Vowels, B. R. et al. 1994. J. Invest. Dermatol. 103:669) suggests that the malignant Th cells in CTCL may be derived from the Th2 subpopulation of CD4+ cells.

Recent studies have shown that excess interleukin-4 production by PBMCs from SzS patients can be inhibited in vitro either by interferon-γ or by interferon-α (Vowels, B. R. et al. 1992. J. Invest. Dermatol. 99:90). Moreover, SzS patients who develop complete remission associated with the disappearance of detectable malignant peripheral blood cells during therapy with biologic response modifiers, including interferon-α, have restored a normal pattern of cytokine production by their PBMC in concert with the normalization of many immune parameters (Vowels, B. R. et al. 1993. J. Invest. Dermatol. 100:556). Therefore, strategies directed simultaneously at affecting the cytokine imbalance and impeding proliferation of the malignant T cell population may have a beneficial effect on the outcome of this frequently fatal disorder.

Interleukin-12 (IL-12) is a cytokine that is a powerful inducer of interferon-γ production and that exerts potent Th1 inducing effects during the evolution of immunologic responses against certain microbial antigens (Chan, S. H. et al. 1991. J. Exp. Med. 173:869–879; Hsieh, C. S. et al. 1993. Science 260:547–549). IL-12 augments Natural Killer (NK) cell cytotoxicity and cytotoxic T cell proliferation and function (Hiramatsu, K. et al. 1998. Cancer Immunol. Immunother. 46:1–6; Haku, T. et al. 1997. Cytokine 9:846–852; Sahin, U. et al. 1996. Cancer Immunol. Immunother. 42:9–1), activities that may be beneficial in regard to the abnormal Th2 clonal proliferation observed in advanced CTCL, including SzS. Studies have shown that PBMCs isolated from patients with advanced CTCL exhibit marked defects in the production of IL-12 (Rook, A. H. et al. 1997. Clin. Exp. Immunol. 107:16–20; Seo, N. et al. 1998. Clin. Exp. Immunol. 112:403–409). Further, IL-12 has been shown to have potent antitumor activity in mice with transplantable and primary tumors (Nishimura et al. 1995. Immunol. Lett. 48:149–152) and in mice with metastatic residual lymphoma (Verbik et al. 1996. Clin. Exp. Metastasis 14:219–229). Brunda and colleagues (1993. J. Exp. Med. 178:1223) have demonstrated antitumor activity of IL-12 in mice following both systemic and intralesional administration.

Recent in vitro experiments have also shown that the depressed interferon-γ production observed in peripheral blood mononuclear cells isolated from patients with advanced CTCL is normalized by the addition of recombinant IL-12. These in vitro studies also showed that the depressed cell-mediated cytotoxicity in CTCL is augmented (Rook, A. H. et al. 1996. Ann. NY Acad. Sci. 795:310–318; Rook et al. 1995. J. Immunol. 154:1491–1498).

It has now been found that advanced CTCL can be successfully treated in humans by in vivo administration of recombinant IL-12.

SUMMARY OF THE INVENTION

An object of the present invention is to provide a method for treating advanced cutaneous T cell lymphoma in humans comprising administering to a human an effective amount of recombinant interleukin-12 so that symptoms of cutaneous T cell lymphoma are reduced.

Another object of the present invention is to provide a combination therapy for treatment of advanced cutaneous T cell lymphoma comprising recombinant interleukin-12 and an adjunct therapeutic agent which stimulates interferon-γ production.

DETAILED DESCRIPTION OF THE INVENTION

Cytokines are intercellular messenger molecules that evoke biological responses after binding to receptors on responsive cells. A variety of cells of the immune system can secrete cytokines, with the principal producers being the T-helper cells (both type 1, Th1, and type 2, Th2) and macrophages. The binding of cytokines to their receptors on responsive cells leads to numerous physiologic responses including the development of cellular and humoral immunity, induction of the inflammatory response, regulation of hematopoiesis, control of cellular proliferation and differentiation, and induction of wound healing. The complexity of the cytokine pathways and the fact that they exhibit cross-regulation, where the cytokines secreted by one subset of Th cells can block production and activity of cytokines secreted by the other subset, has made it difficult to predict the effect of administration of a single cytokine to a patient.

For example, interferon-γ is secreted by the Th1 subset of Th cells, as well as by NK cells. Increases in the level of interferon-γ results in a depression of activity of Th2 cells. IL-12, which is secreted by macrophages and B-cells, can also inhibit activity of Th2 cells. However, IL-10, which is secreted by Th2 cells, results in a decrease in activity of Th1 cells, which secrete interferon-γ. This interrelationship of the cytokine pathways makes it difficult to predict the efficacy of in vivo of administration of a single cytokine in modulating various disease states.

It has now been found, however, that administration of recombinant IL-12 in patients is a safe and effective therapy for advanced CTCL. IL-12 was administered both subcutaneously and intralesionally in a phase I clinical trial of advanced CTCL. A phase I clinical trial is designed to examine both efficacy and safety of a drug.

Patients in the phase I clinical trial were classified as having either extensive plaque (4 patients), SzS (2 patients), or extensive tumors with large cell transformation (2 patients). Patients received either 50, 100, or 300 ng/kg of recombinant IL-12, two times a week for up to 24 weeks. Doses were given both intralesionally and subcutaneously. Subcutaneous dosing resulted in complete responses in 2 of the 4 plaque patients, partial responses in 1 of the 4 plaque patients, and a partial response in 1 of the 2 SzS patients. The overall response rate with subcutaneous dosing (complete and partial responses) was 57%. A minor response was also seen in one of the plaque patients. By "complete response" it is meant complete disappearance of all evidence of disease both clinically and histologically. By "partial response" it is meant that there is at least a 50% decrease (but less than 100%) in size of all measured lesions as compared to their size at the start of therapy. By "minor response" it is meant that there is a 25 to 50% decrease in the size of all measured lesions as compared to their size at the start of therapy.

Following intralesional dosing with recombinant IL-12, individual plaque, erythema, or tumor regression was seen in most patients (8 out of 9); one patient with SzS dropped out of the trial for personal reasons. Biopsy of regressing lesions revealed a marked decrease in the density of the infiltrate in all cases. Increased numbers of cytotoxic T-cells were observed on immunohistochemical analysis in some biopsies.

Adverse effects associated with recombinant IL-12 treatment, either subcutaneously or intralesionally, were minor and included low grade fever and headache. One patient discontinued IL-12 at week 6 due to depression. These results demonstrated that IL-12 was a safe as well as an effective treatment for advanced CTCL. The results showed that IL-12 may augment antitumor responses. The fact the IL-12 was particularly effective in plaque patients was unexpected and unique.

Accordingly, the present invention provides a useful method for alleviating symptoms and treating CTCL in patients which comprises administering recombinant IL-12 to the patient. The method of the present invention is particularly useful in treating advanced CTCL, which includes patients presenting with plaque, Sezary Syndrome, or tumors with large cell transformation. IL-12 can be administered either systemically (e.g., subcutaneously, intravenously) or intralesionally and can be formulated in any pharmaceutically acceptable carrier which is known to those of skill in the art For example, an injectable formulation of recombinant IL-12 is made and sold by Genetics Institute (Cambridge, Mass.). An effective dose of recombinant IL-12 is administered repeatedly, for several weeks, until symptoms of advanced CTCL (such as plaques, tumors or erythroderma) regress or are reduced. An effective dose is one in which there is at least a partial response in the patient. In some patients a reduction of symptoms of advanced CTCL represents a total absence of those lesions after treatment. Dosage schedules and regimens are routinely designed by those of skill based upon results described above for the phase I trial. In a preferred embodiment, approximately 100 to 300 ng/kg of recombinant IL-12 is administered by subcutaneous or intravenous injection 2 to 3 times per week.

The present invention also provides combinational therapies for the treatment of CTCL. It has been found that CTCL may be treated by the combined use of recombinant IL-12 and adjunct therapeutic agents that also induce interferon-γ production. Examples of adjunct therapeutic agents that also induce interferon-γ production include, but are not limited to, retinoids, interleukin-2, interleukin-15, interleukin 18, interferon-α and interferon-γ.

In fact, experiments in peripheral blood monocytes from patients with advanced CTCL indicate that administration of IL-12 in combination with an adjunct therapeutic agent such as interleukin-18 synergistically augment interferon-γ production and cytotoxic lymphocyte activity. In these experiments, PBMC from patients with advanced CTCL and normal healthy volunteers were cultured with medium alone, PHA, interleukin-18 or IL-12 alone, PHA plus interleukin-18 or IL-12, and PHA plus interleukin-18 and IL-12 for 20–48 hours and supernatants were assayed by ELISA for interferon-γ as described by Rook et al. 1995. *J. Immunol.* 154:1491–1498. PBMC were also assayed for NK cell activity using CR51 labeled k562 cells as targets as described by Rook et al. 1995. *J. Immunol.* 154:1491–1498. Interleukin-18 and IL-12 each significantly increased interferon-γ production by patient and normal PBMC. Interferon-γ production was also synergistically augmented by combining interleukin-18 and IL-12 in culture. Similarly cultures combining interleukin-18 and IL-12 more markedly enhanced NK cell activity in comparison to interleukin-18 and IL-12 alone.

Experiments have also shown that clinically available retinoids, such as acitretin, 13-cis-retinoic acid, and all trans-retinoic acid, in concentrations ranging from 1 to 10 ng/ml, induce production of low levels (20 to 100 pg/ml) of interferon-γ in PBMCs from normal volunteers. A number of clinical studies have shown that retinoids have clinical activity in the treatment of CTCL, with response rates ranging from 30% to 60% (Fuss, F. M. and T. M. Kuzel. 1995. *Hematol. Oncol. Clin. North Am.* 9:1127–1137). The highest response rates, however, are seen when patients have early stage disease, not advanced CTCL. Retinoids have been suggested as adjunct therapy for treatment of CTCL with interferons or PUVA. In studies in CTCL patients, the all trans-retinoic acid was the most potent retinoid for inducing interferon-γ activity. Addition of anti-IL-12 neutralizing antibodies to the retinoid-cultured cells reduced the interferon-γ-inducing activity of the retinoids (Rook, A. H. et al. 1996. *Ann NY Acad. Sci.* 795:310–318). Thus, at least a portion of the interferon-γ activity of retinoids appears to be mediated through effects on IL-12. Therefore, patients with advanced CTCL can be administered lower doses of recombinant IL-12 in combination with a clinically available retinoid to alleviate or treat CTCL with fewer side effects from administration of IL-12. Dosages of the retinoid to use in the patients can be selected by one of skill based on clinical use of these drugs for other conditions.

The following nonlimiting examples are provided to further describe the invention.

EXAMPLES

Example 1

Administration of rIL-12 to Humans

This study was an open-label, nonrandomized, single center, Phase ½ study of recombinant human IL-12 administered by subcutaneous injection in patients with cutaneous T-cell lymphoma (CTCL). Adult male and female patients (age≧18 years) with a histological diagnosis of CTCL for whom there wan no standard curative treatment and who met certain inclusion and exclusion criteria were enrolled in the study. Patients were treated on an outpatient basis. However, the initial dose was administered to patients admitted overnight for observation at the Clinical Research Unit. Dose levels of 50 ng/kg, 100 ng/kg and 300 ng/kg were administered two times a week subcutaneously for up to 24 weeks. An initial group of patients was entered at the lower dose (50 ng/kg). Safety at this doses was evaluated for 4 weeks before entering patients at the 100 ng/kg dosing levels. Similarly, an initial group of four patients was entered at the 100 ng/kg dose and safety was evaluated at 4 weeks prior to entering patients at the 300 ng/kg dose range. Total duration of the study was 1 year including 4 months enrollment, maximum 24 weeks of therapy and 2 months follow-up.

What is claimed is:

1. A method for treatment of advanced cutaneous T cell lymphoma in a human comprising administering to a human 100 to 300 ng/ml of recombinant interleukin-12 in a pharmaceutically acceptable carrier and an adjunct therapeutic agent which stimulates interferon-γ production.

* * * * *